United States Patent [19]

Weissman

[11] 4,251,216
[45] Feb. 17, 1981

[54] DENTAL SPLINTING DEVICE

[75] Inventor: Bernard Weissman, New York, N.Y.

[73] Assignee: IPCO Corporation, White Plains, N.Y.

[21] Appl. No.: 116,006

[22] Filed: Jan. 28, 1980

Related U.S. Application Data

[63] Continuation-in-part of Ser. No. 070,247, Aug. 27, 1979.

[51] Int. Cl.³ .............................................. A61C 5/00
[52] U.S. Cl. .................................................... 433/215
[58] Field of Search ........................ 433/225, 229, 215

[56] References Cited

U.S. PATENT DOCUMENTS

| | | | |
|---|---|---|---|
| 3,395,455 | 8/1968 | Overby et al. | 433/225 |
| 3,487,545 | 1/1970 | Weissman | 433/225 |
| 3,822,472 | 7/1974 | Garfinkel | 433/215 |

*Primary Examiner*—Robert Peshock
*Attorney, Agent, or Firm*—Friedman, Goodman & Teitelbaum

[57] ABSTRACT

A dental splinting device includes an elongated bar-like member having a tapered mid-section along its elongated direction, which separates wider end sections to provide a dog bone-like configuration. A substantially flat surface is provided on one face thereof, and four cylindrical members extend perpendicularly from that face. The cylindrical members are received in bores provided in adjacent teeth, with the body member being disposed in a channel extending between the adjacent teeth. The bar-like member has a U-shaped or V-shaped cross sectional configuration. In use, a channel is formed across the adjacent teeth and then bores are formed, preferably using the dental splinting device, in the adjacent teeth registered so as to receive the cylindrical members. The splinting device is then positioned in the channel with the cylindrical members disposed in the bores, and an inlay fills in the channel and covers the splinting device.

17 Claims, 13 Drawing Figures

DENTAL SPLINTING DEVICE

RELATIONSHIP TO OTHER APPLICATIONS

This application is a continuation-in-part application to U.S. Patent Application Ser. No. 070,247 filed on Aug. 27, 1979 by the present inventor and entitled "Dental Retaining Splint". All of the material in the aforementioned copending parent application is herein incorporated by reference.

BACKGROUND OF THE INVENTION

This invention relates to the dental practice in general, and more particularly to a method and apparatus for the reinforcement of dentition in the mouth by means of dental splinting.

The use of dental splints is a highly specialized area of dentistry, and necessitates the use of special dental retaining splints. Most of the prior art devices have limited use, as for example for the lingual surface of anterior teeth, and also require complete procedures often including the formation of a dental impression from a cast model.

An improved dental retaining splint is provided in the aforementioned copending parent application which provides for a dental retaining splint having a bar-like body member with tubular means extending perpendicularly therefrom. The tubular means include axial openings extending therethrough. The body member is fabricated with an H-shaped cross sectional configuration, having the front end rear walls thereof serpentined to define sections therein which can be removed, such as by cutting, to provide a shorter splint. The splint is initially held in a channel formed in adjacent teeth, and the tubular means are utilized as guides for a drill to form pilot holes in the teeth. The pilot holes are then enlarged to form bores which can receive the tubular means. The splint is then repositioned in the channel with the tubular means disposed in the bores and an inlay fills in the channel to cover the splint.

With some teeth, especially the molars, a stronger splint is needed and a greater number of cylindrical members are needed in order to securely hold the teeth in place. Additionally, a larger size splint is required in order to span across the occlusal surfaces of these larger teeth. However, the larger splint may interfere with the spacing between the teeth when the splint has been suitably positioned into the crowns.

SUMMARY OF THE INVENTION

Accordingly, it is an object of the present invention to provide a dental splinting device for the reinforcement and retention of dentition in the mouth, which improves upon existing dental retaining splints.

Another object of the present invention is to provide a dental splinting device which may be utilized with larger dentition, and which will avoid substantial interference with the suitable teeth spacing to thereby provide a minimum amount of discomfort to the patient both in its application and in its use.

A further object of the present invention is to provide a dental splinting device which may be utilized with teeth needing greater support and extra reinforcement.

Still another object of the present invention is to provide a dental splinting device having a bar-like body member with a tapered mid-section along its elongated direction, which separates wider end sections to provide a dog-bone configuration which can be suitably positioned across adjacent teeth and provide secure reinforcement of the teeth while substantially avoiding interference with the space between the teeth.

Yet a further object of the present invention is to provide a dental splinting device having a body portion with a dog-bone configuration along its longitudinal axis, and having a substantially U-shaped or V-shaped cross sectional configuration.

Still a further object of the present invention is to provide a dental splinting device having a body member with four cylindrical members extending perpendicularly therefrom which members can be either solid or tubular.

These objects are achieved in accordance with a preferred embodiment of the present invention, wherein the dental splinting device comprises an elongated bar-like member having a tapered mid-section along its elongated direction, which separates wider end sections to provide a dog bone-like configuration. A substantially flat surface on one face thereof supports four cylindrical members extending perpendicularly therefrom. The cylindrical members are received in bores provided in adjacent teeth with the body member being disposed in a channel extending between the adjacent teeth.

Where the cylindrical members are tubular and include axial openings extending therethrough, the cylindrical members can be utilized for forming the bores. The splinting device is first temporarily held in the channel formed in the adjacent teeth, and the tubular members function as guides for a drill to form pilot holes in the teeth. After the pilot holes are formed, the splint is removed so that the pilot holes function as lead holes for the formation of enlarged bores to receive the tubular members therein for retaining the adjacent teeth in fixed position relative to each other. The splint is then repositioned in the channel with the tubular members disposed in the bores and an inlay fills the channel to cover the splint.

In another embodiment, the cylindrical members can be solid and formed integral with the elongated bar-like member. In this embodiment, the bores are initially formed by means of a separate device which can be either a template, or another dental splinting device having a similar construction provided with supporting tubular members having axial openings therein for guiding a drill during the formation of the bores.

The bar-like member is formed with a U-shaped or V-shaped cross sectional configuration, one surface thereof being flat for supporting the four cylindrical members.

The four cylindrical members can be arranged with respect to an elongated central line so that they are positioned in pairs within the wider end sections. The cylindrical members in each pair can be arranged along a line perpendicular to the elongated central line, or along a line angularly skewed with respect to the elongated central line, or arranged in any other suitable configuration.

BRIEF DESCRIPTION OF THE DRAWINGS

With the above and additional objects and advantages in view, as will hereinafter appear, this invention comprises the devices, combinations, and arrangements of parts hereinafter described by way of example and illustrated in the accompanying drawings of a preferred embodiment in which.

In the various figures of the drawing, like reference characters designate like parts.

DETAILED DESCRIPTION OF THE PREFERRED EMBODIMENT

Figure 1:
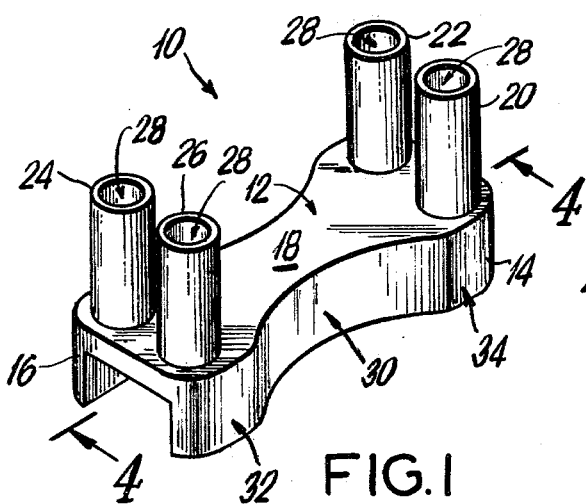
FIG. 1 is a perspective view illustrating the dental splinting device in accordance with the present invention.
Figure 2:
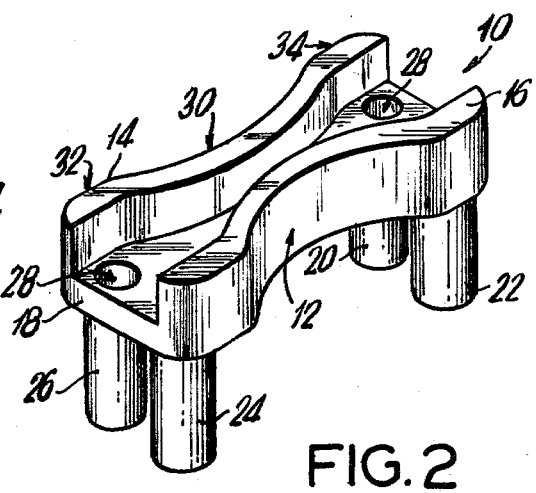
FIG. 2 is another perspective view illustrating the dental splinting device of FIG. 1, facing in an opposite direction of that shown in FIG. 1.

FIGS. 1 and 2 show a dental splinting device 10 in accordance with the present invention. The splinting device includes an elongated bar-like member 12 having a front wall 14, a rear wall 16, and an interconnecting transverse wall 18. The three walls form a U-shaped cross sectional configuration. The outside surface of the wall 18 is substantially flat and supports four upwardly extending cylindrical members 20, 22, 24, 26. Each of the cylindrical members are tubular with an axial opening 28 formed therein and extending through the wall 18, as shown in the cross sectional view of FIG. 4.

The body member 12 has a tapered mid-section 30 along its elongated axis, which separates wider end sections 32 and 34. The cylindrical members are located in pairs in the wider end sections, with the tubular members 20 and 22 being located in the wider end section 34, and the tubular members 24, 26 being located in the wider end section 32. The bar-like body member thereby provides a dog-bone like configuration.

Figure 3:
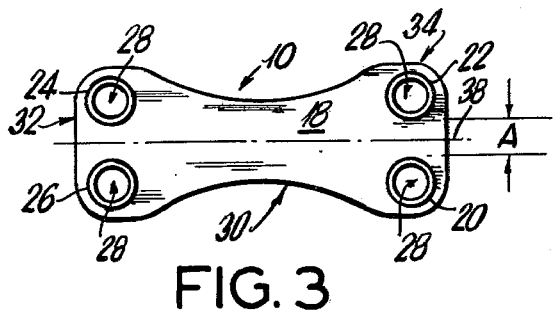
FIG. 3 is a top view of the device as shown in FIG. 1.
Figure 5:
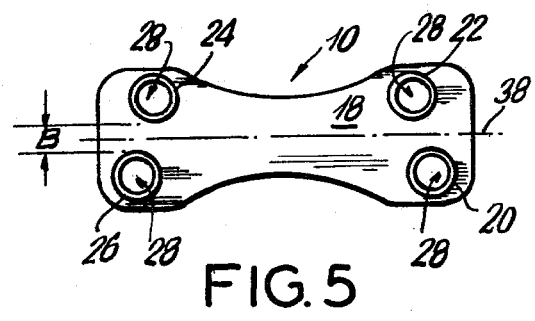
FIGS. 5 and 6 respectively show top views similar to that of FIG. 3, but show modifications of the placement of the cylindrical members.
Figure 6:
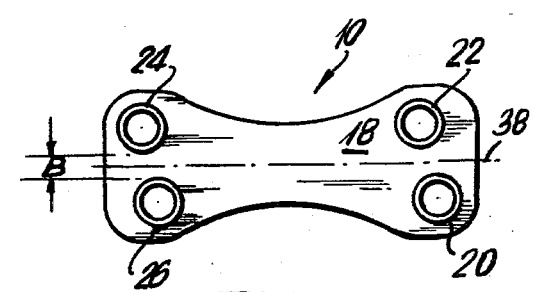

Referring now to FIGS. 3, 5 and 6, the position of the cylindrical members can be modified within the wider end sections. For example in FIG. 3, which shows a top view of FIG. 1, it is noted that the pair of cylindrical members 20, 22, located in the end section 34, are located along a line which is substantially perpendicular to the elongated center line 38. The pair of cylindrical members 24, 26 are similarly situated along a line perpendicular to the elongated center line 38 in the end section 32, shown in FIG. 3. The spacing between the cylindrical body members forming each pair is designated by the distance A.

In FIG. 5 it will be noted that the cylindrical members are again located in pairs with each pair being in a respective wider end section. However, the two cylindrical members 22 and 24, positioned on one side of the elongated center line 38, are longitudinally closer together than the cylindrical members 20 and 26 located on the opposed side of the elongated center line 38. The perpendicular distance between the pair of cylindrical body members 24, 26 is given as the distance B. It should be noted that the perpendicular distance B is less than the perpendicular distance A. However, this is because the distance is taken on a perpendicular line. The length taken along a line interconnecting the two axes of the cylindrical members, however, would be the same both in FIGS. 3 and 5.

In FIG. 6, it is noted that again the positioning of the cylindrical members have been modified. In this case, the cylindrical body members 20, 22 forming one pair, lie along a line which is angularly skewed with respect to the elongated center line 38. The pair of cylindrical members 24, 26 lie along a similar skewed line. Again it should be noted that the perpendicular spacing between the cylindrical members of each pair is designated by the distance B which is again smaller than A. However, again this is because the spacing is taken along a line perpendicular with respect to the elongated center line. However, the fixed distance between the cylindrical members in each pair is substantially the same when taken along a line interconnecting the central axes of the respective cylindrical members. It is noted, that the cylindrical body members can be angularly skewed in an opposite direction of that shown in FIG. 6.

Figure 9:
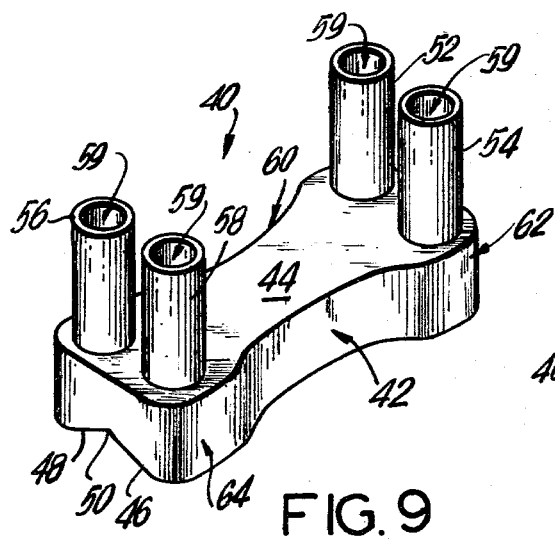
FIG. 9 is a perspective view illustrating another embodiment of the dental splinting device in accordance with the present invention.
Figure 10:
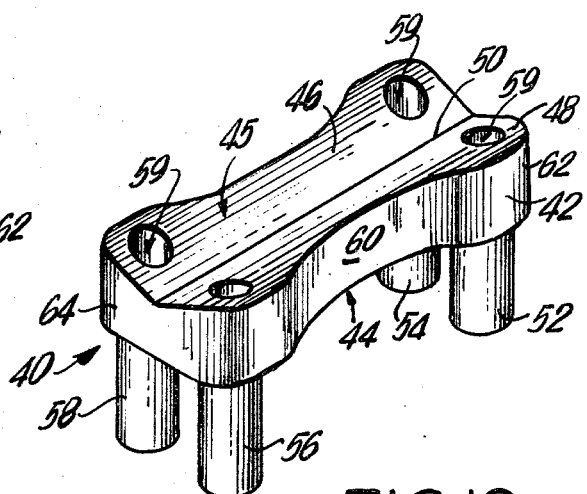
FIG. 10 is another perspective view illustrating the dental splinting device of FIG. 9, facing in an opposite direction of that shown in FIG. 9.

Referring now to FIGS. 9 and 10, there is shown a modification of the dental splinting device. The splinting device 40 is again formed of an elongated bar-like member 42. However, the bar-like member is formed of a solid structure having one surface thereof 44 flattened. The opposing surface 45, as can best be seen in FIG. 10, is formed of two lateral sections 46, 48 spaced on either side of an elongated center line 50 and angularly pitched toward the center line in a direction toward the one surface 44. In this way, the opposing surface 45 has a substantially V-shaped configuration.

Upwardly extending from the flat surface 44, are again provided four cylindrical members 52, 54, 56 and 58, which are perpendicular from the surface 44, and include axial openings 59 therein extending through the bar-like member 42. The bar-like member 42 is formed with a tapered mid-section 60 along its elongated direction separating the wider end sections 62 and 64 to again provide a dog-bone like configuration.

It is noted, that the cylindrical members 52, 54, 56 and 58 can be arranged in the same positions as the cylindrical members 20, 22, 24 and 26, being perpendicular, off-set or angularly skewed with respect to each other as shown in FIGS. 3, 5 and 6.

Figure 11:
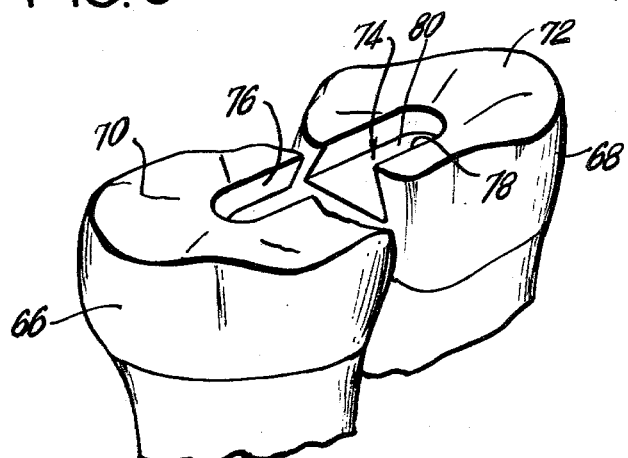
FIG. 11 is a perspective view illustrating two adjacent teeth provided with a channel to receive the dental splinting device of the present invention.
Figure 12:
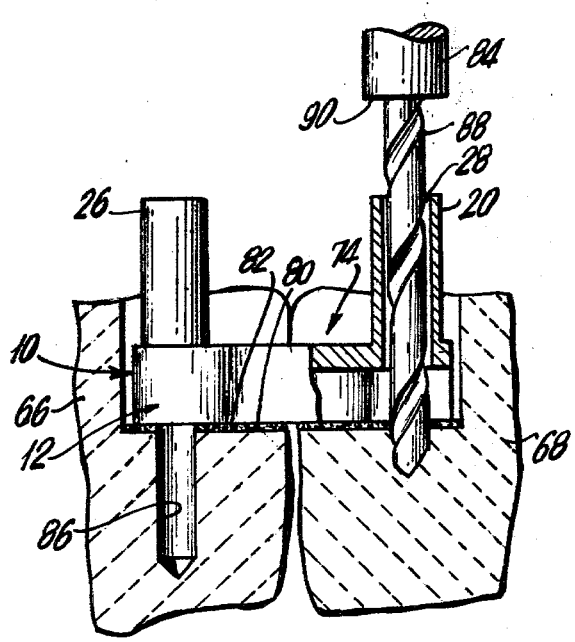
FIG. 12 is an elevational view illustrating the forming of pilot holes in the teeth using the tubular members of the dental splinting device as drilling guides.
Figure 13:
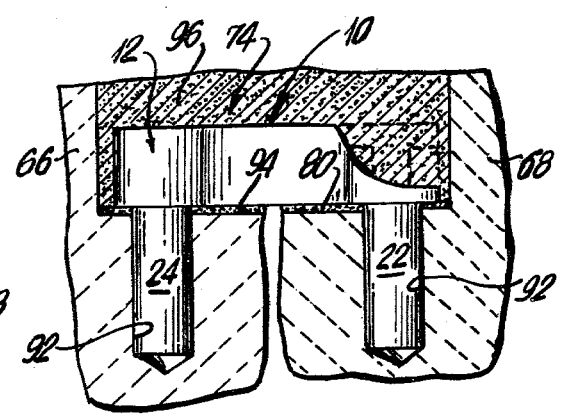
FIG. 13 is an elevational view illustrating the dental splinting device permanently secured in the channel of the teeth with the channel being filled in with suitable dental material.

Referring now to FIGS. 11-13, the operation of the present inventive device will be described. FIG. 11 shows two adjacent teeth 66 and 68, such as for example, the adjacent molars. In each occlusal surface 70, 72 of the crowns, a connecting channel 74 is formed therebetween in a conventional manner. Preferably, the walls 76, 78 of the channel are tapered and provide a wide base 80 at the bottom of the channel where the tapered walls act to retain the inlayed dental material within the wall as will be set forth hereinbelow. It is understood that the channel 74 is oversized to be larger than the bar-like body member 10 or 40, in length, width and height.

After the channel 74 is formed, a layer of temporary adhesive 82 is formed, such as wax or other suitable material, which is disposed on the bottom surface or base 80 of the channel. The splint 10 (or 40) is now positioned in the channel 74 with the tubular members extending outwardly therefrom, being temporarily held by the temporary adhesive 82, as shown in FIG. 12. It is noted that frequently the base 80 of the channel 74 is uneven, so that there may be a tendency for a flat surface disposed thereon to rock. However, since the lower portion of the body member 12 (or 42) is formed in a U-shaped (or V-shaped) configuration, the surface area of contact is limited and, in effect, acts as two legs which are more stable than a flat bar. Furthermore, the spaced provided between the legs of the U-shaped (or V-shaped) configuration permits the subsequent insertion of the dental securing material to provide a greater surface to retain the splint in place. Also, it provides room for the tooth material which is being drilled out to enter into the space without displacing the splint from its temporary position during the drilling operation.

Once the splint device is secured in the channel 74, a pilot drill 84 is inserted successively into each opening of the tubular members and pilot holes 86 are formed in the teeth. Four pilot holes will be formed, two in each of the adjacent teeth. Preferably the drill bit 88 of the pilot drill 84 has a diameter approximately equal to or slightly less than the diameter of the opening 28 (or 59) of the tubular member to that the tubular members function as guides for the drill bit 88. Furthermore, the drill bit 88 has a predetermined length in order to obtain the desired depth of the pilot holes 86. Accordingly, the pilot drill 88 is provided with a stop or an abutment 90 which will contact the upper portion of the tubular members when the desired depth of the pilot holes 86 has been reached.

After the four pilot holes 86 have been made, the splinting device 10 is removed from the channel 80. Another dental drill, not shown, is then used to ream out the holes an enlarge them to form the bores 92 in the teeth. The pilot holes 86 function as lead holes for the enlarging drill bit in the formation of the bores 92.

The splinting device is now ready to be permanently inserted into the bores 92 that are formed. First, a permanent adhesive 94 is disposed on the bottom surface or base 80 of the channel 74. The splint 10 (or 40) is now positioned in the channel 74 with the tubular members disposed in the respective bores 92 provided in the teeth. It should be noted that the enlarging drill bit should have a diameter approximately equal to or slightly larger than the outside diameter of the tubular members so that the bores 92 are large enough to receive the tubular members therein, as is shown in FIG. 13.

Once the splinting device 10 (or 40) is secured in the channel 17, an inlay 96 of dental restorative material, such as precious metal, amalgam, composite resin, ceramic, porcelain, or other suitable material is disposed in the channel 74 over the dental splinting device 10 (or 40) as shown in FIG. 13 to complete the dental procedure. Thus, the tubular members 20, 22, 24 and 26 (or 52, 54, 56 and 58) function to retain the splint 10 (or 40) in position to secure one tooth to its adjacent tooth, and the tapered walls 76, 78 of the channel 74 retain the inlay 96 in the channel to hold the splint 10 (or 40) therein.

The same procedure can be utilized both with regard to the U-shaped cross sectional configuration of the splinting device 10 shown in FIGS. 1–6, as well as the V-shaped configuration of the splinting device 40 shown in FIGS. 9 and 10.

In the embodiments thus far described, the cylindrical members have all been tubular in shape and have therefore, for the most part, served both for the purpose of making the pilot holes which are used as lead holes for the formation of the bores, as well as for forming the stabilizing legs of the splinting member itself. However, as shown in FIGS. 7 and 8, the cylindrical members can be formed of solid material.

Figure 7:
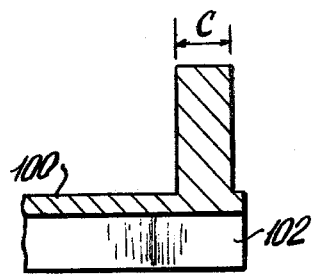
FIGS. 7 and 8 show fragmented sectional views of modifications of the invention utilizing solid cylindrical members.
Figure 8:
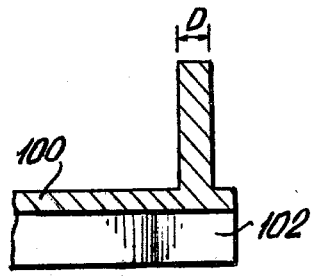

Specifically, in FIG. 7 there is shown a cylindrical leg 98 formed integrally with the body member 100, with FIG. 8 showing a cylindrical leg 99 having a smaller diameter. One of the walls 102 forming the rear face is also shown. It is understood that the structure would be similar to that of any one of the splinting devices 10, 40 shown in FIGS. 1–6, 9 and 10, with the cylindrical members being solid rather than tubular, as is presently shown. With the solid cylindrical members, the splint device itself obviously cannot be utilized for forming the bores. Instead, another device such as the above splinting devices 10, 40, a template, or other means, would initially be used for forming the bores in suitable registration for use with this splinting device having the solid cylindrical members. The holes will be formed and subsequently the splinting device of this type shown in FIGS. 7 and 8 would be inserted into a channel with the cylindrical members 98 or 99 suitably positioned in bores previously prepared to receive these cylindrical members.

Thus, it should be appreciated that two separate devices of the type described, could be utilized. A first one of the devices, such as the splinting devices 10, 40, would have tubular members and would be utilized to initially prepare the holes in the teeth. Subsequently, a second device, of the type shown in FIGS. 7 or 8, having solid cylindrical legs, would then be utilized for the actual splint itself. By using the solid cylindrical leg, the splinting device becomes more secure and will provide a stronger retention hold for the lasting of the splint as well as for the renovation of the teeth.

Figure 4:
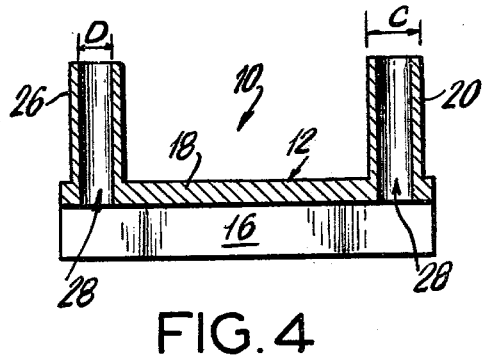
FIG. 4 is a cross sectional view taken along line 4—4 of FIG. 1.

Accordingly, when using the device 10, 40 for forming the holes, in accordance with the operation previously described, the device 10, 40 would be initially positioned in the channel with the tubular members thereof serving as guides for the formation of the holes. It will be noted that the outer diameter of the tubular members, as shown in FIG. 4, is given as C while the inner diameter of these tubular members is provided with the diameter D.

If the splint itself is of the type shown in FIG. 7, where the solid cylindrical members have an outside diameter C, then when using the device 10, 40, initially pilot holes will be formed and subsequently the pilot holes will serve as lead holes in the formation of larger bores whose diameter is C. The cylindrical members 98 of FIG. 7 whose outer diameter is C will then suitabley fit within the bores provided.

However, alternately it is possible to utilize the device 10, 40 and use a drill bit to form holes of a size D. This can be done directly, using the tubular members as the guide for a drill bit in the formation of the holes. Since the diameter of the opening in the tubular members is D, the holes do not have to be enlarged when using a splint of the type shown in FIG. 8. In FIG. 8 the cylindrical members 99 have an outside diameter D. These can easily fit directly into the holes without the necessity of enlarging the holes after they have been formed.

When utilizing the arrangement of the tubular members as shown in FIG. 3, after the axial holes have been formed and widened, the splinting device can be inverted about its elongated axis A, and placed in the channel with the tubular members disposed within the bores provided therefor, as shown in FIG. 13. Similarly, when utilizing the arrangement of the tubular members shown in FIG. 5, the same splinting device which is used for making the holes can also be used as the splint itself. Thus, when using the device arrangement as shown in FIG. 5, the splinting device must be rotated about its transverse axis in order to align the tubular members with the bores provided therefor. However, with the arrangement of the tubular members as shown in FIG. 6, it is not feasible to invert the device and have the tubular members aligned with the bores provided from the same device. Therefore, when using the arrangement shown in FIG. 6, it will be necessary to have two separate devices, one of which is used to form the bores with the particular arrangement as shown, and the second device would serve as the splint. Such second device could either have tubular members or could have solid cylindrical members, as indicated above.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental splinting device comprising, an elongated bar-like body member having a tapered mid-section along its elongated direction, said mid-section being disposed between wider end sections to provide a dogbone like configuration, a substantially flat surface on one face of said bar-like body member, and four cylindrical members extending perpendicularly from said flat surface for being received in bores provided in adjacent teeth with said body member being disposed in a channel extending between the adjacent teeth.

2. A dental splinting device as in claim 1, wherein said cylindrical members have axial holes extending therethrough and through said body members for guiding a drill during formation of pilot holes in the teeth, whereby the pilot holes function as lead holes for the formation of said bores.

3. A dental splinting device as in claim 1, wherein said body member has a front wall, a rear wall, and a base wall interconnecting said front and rear walls to provide a U-shaped cross sectional configuration, said flat surface being disposed on an outside face of said base wall.

4. A dental splinting device as in claim 1, wherein said body member is fabricated from a solid block of material and includes a second face opposing said one face of said body member, said second face including two lateral sections with one section disposed on either side of an elongated center line, said lateral sections being inwardly pitched towards said elongated center line to provide a V-shaped configuration, and a peripheral wall around said body member being substantially perpendicular to said flat surface of said one face.

5. A dental splinting device as in claim 1, wherein said four cylindrical members are divided into two pairs with one pair being respectively located in each of said wider end sections.

6. A dental splinting device as in claim 5, wherein the cylindrical members within each pair are equally spaced on either side of an elongated center line and are separated from each other by a fixed distance therebetween.

7. A dental splinting device as in claim 6, wherein the cylindrical members in each pair lie along a line perpendicular to the elongated center line, said body member being symmetrical both in an elongated direction and a transverse direction.

8. A dental splinting device as in claim 6, wherein the cylindrical members disposed on one side of the elongated center line are longitudinally closer to each other than the cylindrical members disposed on the other side of the elongated center line.

9. A dental splinting device as in claim 6, wherein the cylindrical members in each pair respectively lie along a line skewed at a given angle with respect to the elongated center line.

10. A dental splinting device as in claim 1, wherein said cylindrical members are solid members.

11. A dental splinting device as in claim 10, and further comprising a bore forming device for providing the bores in the adjacent teeth, said bore forming device comprising a base member and tubular members extending perpendicularly therefrom, said tubular members including axial openings extending therethrough for guiding a drill during formation of holes in the teeth.

12. A dental splinting device as in claim 11, wherein the diameter of said axial openings is proximately equal to the outer diameter of said cylindrical members, whereby the holes drilled function as the bores in the teeth.

13. A dental splinting device as in claim 11, wherein the outer diameter of said cylindrical members is substantially equal to the outer diameter of the tubular members, whereby the holes drilled function as lead holes for the formation of said bores in the teeth.

14. A method for reinforcing dentition, said method comprising;
   forming a channel across at least two adjacent teeth;
   drilling four bores in a base wall of the channel;
   inserting a splinting member, having a body portion with four cylindrical members extending therefrom, into said channel with said cylindrical members being positioned into said bores in the teeth; and
   filling the channel and covering the splinting member with a dental material.

15. A method according to claim 14, including making said cylindrical members tubular with axial openings therethrough, and wherein said step of drilling further comprises the steps of:
   temporarily disposing the splinting member in said channel across the adjacent teeth with said cylindrical members extending outwardly from said channel and with two cylindrical members being disposed on each tooth;
   drilling pilot holes in the two teeth by using the axial openings as guides for the drilling;
   removing the splinting member from the channel, and enlarging the pilot holes to form the bores with the pilot holes functioning as lead holes for the bores.

16. A method according to claim 15, including arranging said cylindrical members in pairs on either side of an elongated center line extending across the body portion with the cylindrical members fixed on one side of the elongated center line being longitudinally closer to each other than the cylindrical members fixed on the other side of the elongated center line, and further comprising the step of rotating said splinting members about its transverse axis after its use to form the pilot holes in order to dispose the cylindrical members into the bores prior to said filling of said channel.

17. A method according to claim 14, including making said cylindrical members of solid material, and further comprising using hole forming means to accurately locate the bores in the teeth for receiving said cylindrical members.

* * * * *